(12) United States Patent
Geelan et al.

(10) Patent No.: US 6,344,560 B1
(45) Date of Patent: Feb. 5, 2002

(54) NITROAROMATIC SOLUBILIZER FOR NITROXYLS IN AROMATIC SOLVENTS

(75) Inventors: Brendan J. Geelan, East Haven; Brigitte Benage, Wolcott; Gerald J. Abruscato, Southington; Kirk A. Schlup, Woodbury; Ruben S. Grewal, Oakville; Andrew J. Eisenstein, Southbury, all of CT (US)

(73) Assignee: Uniroyal Chemical Company, Inc., Middlebury, CT (US)

( * ) Notice: Subject to any disclaimer, the term of this patent is extended or adjusted under 35 U.S.C. 154(b) by 0 days.

(21) Appl. No.: 09/564,221

(22) Filed: May 3, 2000

(51) Int. Cl.$^7$ .............................. C07F 9/06; C07F 9/02; C07D 211/36; C07D 223/10; C07C 205/00

(52) U.S. Cl. ........................ 546/21; 546/22; 546/242; 540/485; 540/487; 548/412; 548/413; 548/542; 568/927

(58) Field of Search ................................ 540/485, 487; 546/21, 22, 242; 548/412, 413, 542; 568/927

(56) References Cited

U.S. PATENT DOCUMENTS

| | | | |
|---|---|---|---|
| 2,304,728 A | 12/1942 | Boyer et al. ................. 260/669 |
| 3,163,677 A | 12/1964 | Hoffman et al. ............ 260/583 |
| 3,334,103 A | 8/1967 | Feldman et al. ............ 260/290 |
| 3,373,182 A | 3/1968 | Hoffmann et al. ........ 260/465.5 |
| 3,422,144 A | 1/1969 | Hoffmann et al. .......... 260/570 |
| 3,502,692 A | 3/1970 | Feldman et al. ......... 260/326.3 |
| 3,873,564 A | 3/1975 | Schneider et al. ....... 260/309.6 |
| 3,966,711 A | 6/1976 | Rasberger ................. 260/239.3 |
| 4,105,506 A | 8/1978 | Watson .......................... 203/9 |
| 4,182,658 A | 1/1980 | Watson .......................... 203/9 |
| 4,252,615 A | 2/1981 | Watson .......................... 203/9 |
| 4,434,307 A | 2/1984 | Miller ............................ 585/4 |
| 4,439,278 A | 3/1984 | Douglas et al. ................ 203/9 |
| 4,466,904 A | 8/1984 | Watson et al. .............. 252/482 |
| 4,466,905 A | 8/1984 | Butler et al. ................. 252/403 |
| 4,468,343 A | 8/1984 | Butler et al. ................. 252/403 |
| 4,558,169 A | 12/1985 | Watson et al. .............. 585/440 |
| 4,664,845 A | 5/1987 | Jancis et al. ................ 252/401 |
| 4,665,185 A | 5/1987 | Winter et al. ............... 546/184 |
| 4,692,544 A | 9/1987 | Goerner et al. ................. 560/4 |
| 4,720,566 A | 1/1988 | Martin ........................ 558/306 |
| 4,774,374 A | 9/1988 | Abruscato et al. ............. 585/24 |
| 4,797,504 A | 1/1989 | Roling ........................... 560/4 |
| 4,912,247 A | 3/1990 | Roling ........................ 558/306 |
| 4,929,778 A | 5/1990 | Roling ........................... 585/3 |
| 5,128,022 A | 7/1992 | Reid ............................ 208/48 |
| 5,254,760 A | 10/1993 | Winter et al. .................. 585/5 |
| 5,446,220 A | 8/1995 | Arhancet ....................... 585/5 |
| 5,545,782 A | 8/1996 | Winter et al. .................. 585/5 |
| 5,545,786 A | 8/1996 | Winter et al. ............... 585/435 |
| 5,648,574 A | 7/1997 | Arhancet et al. .............. 585/5 |
| 5,711,767 A | 1/1998 | Gande et al. ................. 44/423 |
| 5,907,071 A | 5/1999 | Arhancet ....................... 585/5 |
| 5,910,232 A | 6/1999 | Hyde et al. .................... 203/9 |

FOREIGN PATENT DOCUMENTS

| | | |
|---|---|---|
| EP | 0 178 168 A2 | 10/1985 |
| EP | 0325059 A2 | 12/1988 |
| EP | 0398633 A1 | 5/1990 |
| EP | 0594341 A1 | 10/1993 |
| EP | 0 765 856 A1 | 4/1997 |
| FR | 2761060 | 3/1989 |
| GB | 1127127 | 4/1966 |
| SU | 478838 | 7/1975 |
| SU | 334845 | 1/1984 |
| WO | 97/46504 | 12/1997 |
| WO | 98/02403 | 1/1998 |
| WO | 98/14416 | 4/1998 |
| WO | 98/25872 | 6/1998 |
| WO | 99/20584 | 4/1999 |

*Primary Examiner*—Mukund J. Shah
*Assistant Examiner*—Tamthom N. Truong
(74) *Attorney, Agent, or Firm*—Daniel Reitenbach; Paul Grandinetti

(57) ABSTRACT

A nitroaromatic compound is used to enhance the solubility of a nitroxyl compound in an aromatic hydrocarbon solvent.

13 Claims, No Drawings

NITROAROMATIC SOLUBILIZER FOR NITROXYLS IN AROMATIC SOLVENTS

BACKGROUND OF THE INVENTION

1. Field of the Invention

The present invention is directed to the use of at least one nitroaromatic compound to enhance the solubility of at least one nitroxyl compound in aromatic hydrocarbon solvents.

2. Description of Related Art

Many ethylenically unsaturated monomers undesirably polymerize at various stages of their manufacture, processing, handling, storage, and use. A particularly troublesome problem is equipment fouling caused by polymerization in the purification stages of the production processes of such monomers. Polymerization, such as thermal polymerization, during their purification results in the loss of the monomer and a loss in production efficiency owing to the deposition of polymer in or on the equipment being used in the purification, the deposits of which must be removed from time to time. Additionally, the formation of soluble polymer leads to loss of monomer, i.e., a lower yield, and an increase in the viscosity of any tars that may be produced. The processing of the tars then requires higher temperature and work (energy cost) to remove residual monomer.

Nitroxyls are very efficient polymerization inhibitors for use in the purification of vinyl aromatic monomers. Many of these nitroxyls are solids at ambient conditions. Dosing of a solid inhibitor into a monomer purification train, usually a continuous distillation process, is difficult and can be a safety hazard, owing to the easy plugging of solids dosing systems. The solvents commonly used to add inhibitors into a distillation train for vinyl aromatics are the vinyl aromatic monomers themselves or the corresponding saturated vinyl compounds, i.e. styrene or ethylbenzene, or divinylbenzene or diethylbenzene. These solvents are highly flammable and potentially carcinogenic. Therefore, safety (and economic) concerns require that the solutions be made as concentrated as possible in these flammable solvents. Unfortunately, many nitroxyls have very limited solubilities in these solvents.

U.S. Pat. No. 3,163,677 discloses N,N,O-trisubstituted hydroxylamines and N,N-disubstituted nitroxides of the formulae:

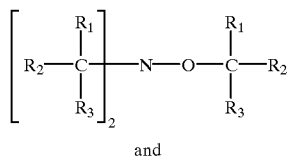

and

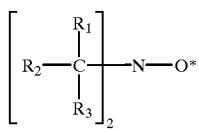

wherein $R_1$, $R_2$, and $R_3$ are each an all radical having 1 to 15 carbon atoms. (As used herein, the designation N—O* denotes a stable free radical wherein the asterisk is an unpaired electron.) The N,N,O-trisubstituted hydroxylamines can be used to make the N,N-disubstituted nitroxides, which are stable free radicals and are said to be useful as polymerization inhibitors.

U.S. Pat. No. 3,334,103 discloses that nitroxides can be prepared from the corresponding heterocyclic amine wherein the nitrogen atom of the nitroxide group is attached to other than a tertiary carbon of an aliphatic group (i.e., the nitrogen atom forms a part of a heterocyclic nucleus). These nitroxides are said to have useful properties similar to those described for the N,N-disubstituted nitroxides of U.S. Pat. No. 3,163,677.

U.S. Pat. No. 3,372,182 discloses that a great variety of N,N-disubstituted, stable, free radical nitroxides not otherwise readily available can be prepared by a simple and convenient process that comprises pyrolyzing in an inert reaction medium virtually any hydroxylamine that is susceptible to cleavage of the O—C bond, e.g., tri-t-butylhydroxylamine.

U.K. Patent Number 1,127,127 discloses that acrylic acid can be stabilized against polymerization by the addition thereto of a nitroxide having the essential skeletal structure:

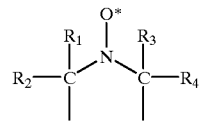

wherein $R_1$, $R_2$, $R_3$, and $R_4$ are alkyl groups and no hydrogen is bound to the remaining valencies on the carbon atoms bound to the nitrogen. The two remaining valencies that are not satisfied by $R_1$ to $R_4$ or nitrogen can also form part of a ring (e.g., 2,2,6,6-tetramethyl-4-hydroxy-piperidine-1-oxyl).

U.S. Pat. No. 3,422,144 discloses stable, free radical nitroxides of the formula:

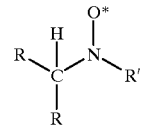

wherein R is selected from the group consisting of tertiary alkyl, aryl, alkaryl, haloaryl, carboxyaryl, alkoxyaryl, alkylthioaryl, pyridyl, and dialkylaminoaryl, and R' is tertiary alkyl. These nitroxides are said to be useful as traps for reactive free radicals both in the counting of free radicals and for inhibiting oxidation and free radical polymerization.

U.S. Pat. No. 3,494,930 discloses free radicals of the nitroxide type for use as initiators of free radical reactions, collectors of free radicals, polymerization inhibitors or antioxidants. They are constituted by nitrogenous bicyclic compounds in which one of the bridges comprises solely the nitroxide radical group and, in particular, by aza-9-bicyclo (3,3,1)nonanone-3-oxyl-9, and by aza-9-bicyclo(3,3,1) nonane oxyl-9.

U.S. Pat. No. 3,873,564 discloses compounds and a method for assaying enzymes by adding to a medium containing an enzyme a stable free radical compound having a stable free radical functionality which, when subjected to an enzyme-catalyzed reaction, changes the environment of the free radical functionality. By following the is change in the electron spin resonance spectrum as affected by the change in environment, the type of enzyme and the activity of the enzyme can be determined. The compounds found useful are normally stable nitroxide radicals with an enzyme labile functionality. Other compounds include two cyclic nitroxide containing rings joined by a chain having an enzyme labile functionality.

U.S. Pat. No. 3,966,711 teaches that 2,2,7,7-tetraalkyl- and 2,7-dispiroalkylene-5-oxo-1,4-diazacycloheptanes substituted in the 4-position by mono- or tetravalent radicals are powerful light-stabilizers for organic polymers. They are said to possess higher compatibility than their 4-unsubstituted homologues, from which they can be synthesized by reactions known for N-alkylation. Preferred substituents in the 4-position are alkyl, alkylene, alkenyl, aralkyl, and esteralkyl groups. The 1-nitroxyls derived from the imidazolidines by oxidation with hydrogen peroxide or percarboxylic acids are also said to be good light stabilizers.

U.S. Pat. No. 4,182,658 discloses a method for preventing the polymerization of a readily polymerizable vinyl aromatic compound during distillation at elevated temperatures within a distillation apparatus that is subject to an emergency condition, such as a power outage. This method comprises force-feeding a supplemental polymerization inhibitor having a high solubility in the vinyl aromatic compound and a long duration of efficiency into each of the distillation vessels of a conventional distillation apparatus in an amount sufficient to prevent polymerization therein.

U.S. Pat. No. 4,664,845 discloses compositions, comprised of a dinitrophenol in an aromatic hydrocarbon solvent, which compositions further comprise a sufficient amount of a phenylenediamine such that a greater amount of dinitrophenol is in solution than would be present in solution if such phenylenediamine were not present, that exhibit unexpectedly desirable low temperature stability, and may be diluted with additional solvent to be employed as polymerization inhibitors for vinyl aromatic compounds.

U.S. Pat. No. 4,665,185 discloses a process for the efficient preparation of nitroxyls of sterically hindered amines by the oxidation of the amine using a hydroperoxide in the presence of a small amount of a metal ion catalyst, at moderate temperature for a short period of time, to give the nitroxyl in high yield and purity.

U.S. Pat. No. 5,254,760 teaches that the polymerization of a vinyl aromatic compound, such as styrene, is very effectively inhibited during distillation or purification by the presence of at least one stable nitroxyl compound together with at least one aromatic nitro compound.

U.S. Pat. Nos. 5,545,782 and 5,545,786 disclose that nitroxyl inhibitors in combination with some oxygen reduce the premature polymerization of vinyl aromatic monomers during the manufacturing processes for such monomers. Even small quantities of air used in combination with the nitroxyl inhibitors are said to result in vastly prolonged inhibition times for the monomers.

U.S. Pat. No. 5,711,767 discloses that the use of nitroxide compounds alone or in combination with aromatic amines, such as substituted phenylenediamines, or phenolic antioxidants provides an effective way to prevent oxidative degradation and gum formation in gasolines.

U.S. Pat. No. 5,910,232 teaches that inhibition performance in styrene is processing is improved through the addition of a stable nitroxide free radical compound to the styrene feed and to the reflux of at least one column. A non-toxic retarder, such as phenylenediamine, may also optionally be added to the styrene feed and to the reflux.

European Patent Application 0 178 168 A2 discloses a method for inhibiting the polymerization of an $\alpha,\beta$-ethylenically unsaturated monocarboxylic acid during its recovery by distillation by using a nitroxide free radical.

European Patent Application 0 765 856 A1 discloses a stabilized acrylic acid composition in which the polymerization of the acrylic acid is inhibited during the distillation process for purifying or separating the acrylic acid as well as during transport and storage. The compositions comprise three components: (a) acrylic acid, (b) a stable nitroxyl radical, and (c) a dihetero-substituted benzene compound having at least one transferable hydrogen (e.g., a quinone derivative such as the monomethyl ether of hydroquinone (MEHQ)). During the distillation process, transport, and storage, components (b) and (c) are present in a polymerization-inhibiting amount. During the distillation process, oxygen (d) is preferably added with components (b) and (c).

WO 97/46504 concerns substance mixtures containing: (A) monomers containing vinyl groups; and (B) an active amount of a mixture which inhibits premature polymerization of the monomers containing vinyl groups during their purification or distillation and contains: (i) between 0.05 and 4.5 wt %, relative to the total mixture (B), of at least one N-oxyl compound of a secondary amine which has no hydrogen atom at the $\alpha$-C atoms; and (ii) between 99.95 and 95.5 wt % relative to the total mixture (B), of at least one nitro compound. The publication also discloses a process for inhibiting the premature polymerization of monomers, and the use of mixture (B) for inhibiting the premature polymerization of monomers.

WO 98/14416 discloses that the polymerization of vinyl aromatic monomers such as styrene is inhibited by the addition of a composition of a stable hindered nitroxyl radical and an oxime compound.

WO 98/25872 concerns substance mixtures containing: (A) compounds containing vinyl groups; (B) an active amount of a mixture which inhibits premature polymerization of the compounds containing vinyl groups and contains: (i) at least one N-oxyl compound of a secondary amine which does not carry any hydrogen atoms on the $\alpha$-carbon atoms; and (ii) at least one iron compound; (C) optionally nitro compounds; and (D) optionally co-stabilizers. The publication also discloses a process for inhibiting the premature polymerization of compounds (A) containing vinyl groups, and the use of (B) optionally mixed with nitro compounds (C) and/or co-stabilizers (D) for inhibiting the premature polymerization of radically polymerizable compounds and stabilizing organic materials against the harmful effect of radicals.

WO 99/20584 discloses that polymerization can be inhibited during the anaerobic production of styrene through the addition of a combination of a stable nitroxide free radical compound and a non-toxic phenylenediamine compound.

CS-260755B 1 is directed to the preparation of 4-substituted-2,2,6,6-tetramethylpiperidine nitroxyls as olefin stabilizers.

SU-334845 A1 is directed to the inhibition of the radical polymerization of oligoester acrylates using iminoxyl radical inhibitors of a given formula.

SU-478838 is directed to the inhibition of the radical polymerization of oligoester acrylates and the prevention of oligomeric peroxides using a binary polymerization inhibitor comprising quinone.

FR 2,761,060 relates to the prevention of premature polymerization of styrene during its production by dehydrogenation of ethylbenzene by injecting into the process effluent a radical inhibitor based on an oxyl-tetramethylpiperidine derivative.

The foregoing are incorporated herein by reference in their entirety.

SUMMARY OF THE INVENTION

As used herein, the abbreviation TEMPO stands for 2,2,6,6-tetramethyl-1-piperidinyloxy. Thus, 4-amino-TEMPO is 4-amino-2,2,6,6-tetramethyl-1-piperidinyloxy; 4-hydroxy-TEMPO is 4-hydroxy-2,2,6,6-tetramethyl-1- piperidinyloxy (also known in the art as HTEMPO); 4-oxo-TEMPO is 4-oxo-2,2,6,6-tetramethyl-1-piperidinyloxy; and so on.

Nitroaromatics and nitroxyls are known polymerization inhibitors. Since nitroxyls are considered true inhibitors, they are often used with nitrophenol compounds (retarders) to provide protection in the case of failure in the inhibitor feed system of a monomer manufacturing plant.

It has now been found that the addition of a nitroaromatic to a nitroxyl compound in an aromatic hydrocarbon solvent enhances the solubility of the nitroxyl in the aromatic solvent, enabling production and shipment of a more concentrated solution of the nitroxyl in the aromatic solvent. The nitroaromatic is also a known polymerization inhibitor, and as such, is a useful additive to the purification train as well. Thus the blend of nitroaromatic/nitroxyl/aromatic solvent can be added directly to the purification train of the vinyl aromatic monomer, or the blend can be further diluted to enable better control of dosing of the inhibiting system.

More particularly, the present invention is directed to a method for increasing the solubility of an compound having the structural formula:

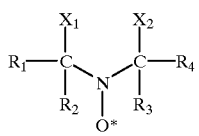

(I)

in an aromatic hydrocarbon solvent comprising adding to said solvent a nitroaromatic having the structure:

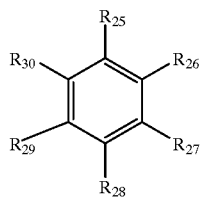

II wherein $R_{25}$, $R_{26}$, $R_{27}$, $R_{28}$, $R_{29}$, and $R_{30}$, are independently selected from the group consisting of hydrogen, alkyl, aryl, cycloalkyl, heterocyclic, substituted alkyl, substituted aryl, $OR_{11}$, $NR_{11}R_{12}$, $SR_{11}$, $NO_2$, NO, CN, $COR_{11}$, $COOR_{11}$, $CONR_{11}R_{12}$, $NR_{11}COR_{12}$, halogen (as used herein, halogen includes fluorine, chlorine, bromine, and iodine), and/or any two adjacent groups can be taken together to form ring structure(s) of five to seven members, provided that at least one of $R_{25}$, $R_{26}$, $R_{27}$, $R_{28}$, $R_{29}$, and $R_{30}$ is $NO_2$, and $R_{11}$, and $R_{12}$ are independently selected from the group consisting of hydrogen, alkyl, aryl, benzyl, cyclic, heterocyclic, and substituted alkyl or aryl where the substituents are C, O, N, S, or P, or $R_{11}$ and $R_{12}$ can be taken together to form a ring structure of five to seven members. Nitroaromatic compounds useful in the practice of the present invention have been described in U.S. Pat. No. 5,254,760.

In formula (I), $R_1$ and $R_4$ are independently selected from the group consisting of hydrogen, alkyl, and heteroatom-substituted alkyl and $R_2$ and $R_3$ are independently selected from the group consisting of alkyl and heteroatom-substituted alkyl; and $X_1$ and $X_2$ (1) are independently selected from the group consisting of halogen, cyano, $COOR_7$, —S—$COR_7$, —$OCOR_7$, (wherein $R_7$ is alkyl or aryl), amido, —S—$C_6H_5$, carbonyl, alkenyl, or alkyl of 1 to 15 carbon atoms, or (2) taken together, form a ring structure with the nitrogen, preferably of five, six, or seven members.

The present invention is directed preferably to a method for increasing the solubility of a compound having the structural formula:

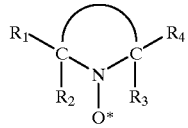

wherein $R_1$ and $R_4$ are independently selected from the group consisting of hydrogen, alkyl, and heteroatom-substituted alkyl and $R_2$ and $R_3$ are independently selected from the group consisting of alkyl and heteroatom-substituted alkyl, and the

portion represents the atoms necessary to form a five-, six-, or seven-membered heterocyclic ring, in an aromatic hydrocarbon solvent comprising adding to said solvent a nitroaromatic having the structure:

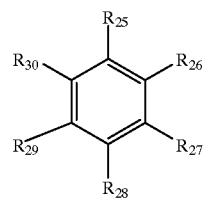

II wherein $R_{25}$, $R_{26}$, $R_{27}$, $R_{28}$, $R_{29}$, and $R_{30}$, are independently selected from the group consisting of hydrogen, alky, aryl, cycloalkyl, heterocyclic, substituted alkyl, substituted aryl, $OR_{11}$, $NR_{11}R_{12}$, $SR_{11}$, $NO_2$, NO, CN, $COR_{11}$, $COOR_{11}$, $CONR_{11}R_{12}$, $NR_{11}COR_{12}$, halogen (as used herein, halogen includes fluorine, chlorine, bromine, and iodine), and/or any two adjacent groups can be taken together to form ring structure(s) of five to seven members, provided that at least one of $R_{25}$, $R_{26}$, $R_{27}$, $R_{28}$, $R_{29}$, and $R_{30}$ is $NO_2$, and $R_{11}$, and $R_{12}$ are independently selected from the group consisting of hydrogen, alkyl, aryl, benzyl, cyclic, heterocyclic, and substituted alkyl or aryl where the substituents are C, O, N, S, or P, or $R_{11}$ and $R_{12}$ can be taken together to form a ring structure of five to seven members.

The atoms necessary to complete the rings referred to above are preferably carbon atoms, but heteroatoms, such as O, N, P, or S, may also be present.

DESCRIPTION OF THE PREFERRED EMBODIMENTS

As stated above, in one preferred aspect, the present invention is directed to a method for increasing the solubility of a compound having the structural formula:

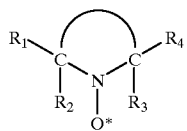

wherein $R_1$ and $R_4$ are independently selected from the group consisting of hydrogen, alkyl, and heteroatom-substituted alkyl and $R_2$ and $R_3$ are independently selected from the group consisting of alkyl and heteroatom-substituted alkyl, and the

portion represents the atoms necessary to form a five-, six-, or seven-membered heterocyclic ring, in an aromatic hydrocarbon solvent comprising adding to said solvent a nitroaromatic having the structure:

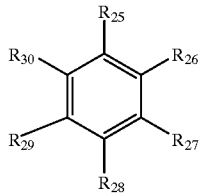

II wherein $R_{25}$, $R_{26}$, $R_{27}$, $R_{28}$, $R_{29}$, and $R_{30}$, are independently selected from the group consisting of hydrogen, alkyl, aryl, cycloalkyl, heterocyclic, substituted alkyl, substituted aryl, $OR_{11}$, $NR_{11}R_{12}$, $SR_{11}$, $NO_2$, NO, CN, $COR_{11}$, $COOR_{11}$, $CONR_{11}R_{12}$, $NR_{11}COR_{12}$, halogen (as used herein, halogen includes fluorine, chlorine, bromine, and iodine), and/or any two adjacent groups can be taken together to form ring structure(s) of five to seven members, provided that at least one of $R_{25}$, $R_{26}$, $R_{27}$, $R_{28}$, $R_{29}$, and $R_{30}$ is $NO_2$, and $R_{11}$ and $R_{12}$ are independently selected from the group consisting of hydrogen, alkyl, aryl, benzyl, cyclic, heterocyclic, and substituted alkyl or aryl where the substituents are C, O, N, S, or P, or $R_{11}$ and $R_{12}$ can be taken together to form a ring structure of five to seven members.

Accordingly, one of the several classes of cyclic nitroxides that can be employed in the practice of the present invention can be represented by the following structural formula:

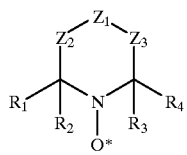

wherein $R_1$, $R_2$, $R_3$, and $R_4$ are as described above and $Z_1$, $Z_2$, and $Z_3$ are independently selected from the group consisting of oxygen, sulfur, secondary amines, tertiary amines, phosphorus of various oxidation states, and substituted or unsubstituted carbon atoms, such as $>CH_2$, $>CHCH_3$, $>C=O$, $>C(CH_3)_2$, $>CHBr$, $>CHCl$, $>CHI$, $>CHF$, $>CHOH$, $>CHCN$, $>C(OH)CN$, $>CHCOOH$, $>CHCOOCH_3$, $>CHCOOC_2H_5$, $>C(OH)COOC_2H_5$, $>C(OH)COOCH_3$, $>C(OH)CHOHC_2H_5$, $>CNR_5R_6$, $>CCONR_5R_6$, $>C=NOH$, $>C=CH—C_6H_5$, $>CF_2$, $>CCl_2$, $>CBr_2$, $>CI_2$, $>CPR_{13}R_{14}R_{15}$, and the like, where $R_5$ and $R_6$ are independently selected from the group consisting of hydrogen, alkyl, aryl, and acyl and $R_{13}$, $R_{14}$, and $R_{15}$ are independently selected from the group consisting of unshared electrons, alkyl, aryl, =O, $OR_{16}$, and $NR_{17}R_{18}$, where $R_{16}$, $R_{17}$, and $R_{18}$, are independently selected from the group consisting of hydrogen, alkyl, and aryl. Where $R_5$ and/or $R_6$ are alkyl, it is preferred that they be a lower alkyl (i.e., one having one to four carbon atoms, e.g., methyl, ethyl, propyl, butyl, and isomers thereof).

Where $R_5$ and/or $R_6$ are aryl, it is preferred that they be aryl of from 6 to 10 carbon atoms, e.g., phenyl or naphthyl, which, in addition, may be substituted with non-interfering substituents, e.g., lower alkyl groups, halogens, and the like.

Where $R_5$ and/or $R_6$ are acyl, it is preferred that they be acyl of the structure

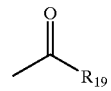

where $R_{19}$ is alkyl, aryl, $OR_{20}$, or $NR_{20}R_{21}$ and where $R_{20}$ and $R_{21}$ are alkyl, aryl, or

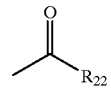

where $R_{22}$ is alkyl or aryl. Where $R_{19}$, $R_{20}$, $R_{21}$, or $R_{22}$ are alkyl, they are preferably alkyl of from 1 to 15 carbon atoms, more preferably lower alkyl of from 1 to 4 carbon atoms, as described above. Where $R_{19}$, $R_{20}$, $R_{21}$, or $R_{22}$ are aryl, they are preferably aryl of from 6 to 10 carbon atoms, as described above.

Another of the several classes of cyclic nitroxides that can be employed in the practice of the present invention can be represented by the following structural formula:

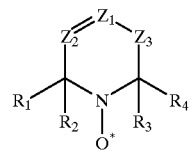

wherein $R_1$, $R_2$, $R_3$, and $R_4$ are as described above and $Z_1$ and $Z_2$, which may be the same or different, are nitrogen or substituted or unsubstituted carbon atoms, such as =C(H)—, =C(CH_3)—, =C(COOH)—, =C(COOCH_3)—, =C(COOC_2H_5)—, =C(OH)—, =C(CN)—, =C(NR_5R_6)—, =C(CONR_5R_6)—, and the like, and where $Z_3$, $R_5$, and $R_6$ are as described above.

The cyclic nitroxides employed in the practice of the present invention can also be derived from five-membered rings. These compounds are of the structure:

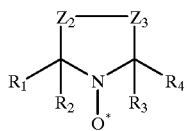

wherein $R_1$, $R_2$, $R_3$, and $R_4$ are as described above and $Z_2$ and $Z_3$, which may be the same or different, are sulfur, oxygen, primary amines, secondary amines, phosphorus of various oxidation states, or substituted or unsubstituted carbon atoms, such as, >$CH_2$, >$CHCH_3$, >C=O, >$C(CH_3)_2$, >CHBr, >CHCl, >CHI, >CHF, >CHOH, >CHCN, >C(OH)CN, >CHCOOH, >CHCOOCH$_3$, >CHCOOC$_2$H$_5$, >C(OH)COOC$_2$H$_5$, >C(OH)COOCH$_3$, >C(OH)CHOHC$_2$H$_5$, >C(NR$_5$R$_6$)—, >C(CONR$_5$R$_6$)—, >C=NOH, >C=CH—C$_6$H$_5$, >CF$_2$, >CCl$_2$, >CBr$_2$, >CI$_2$, >CPR$_{13}$R$_{14}$R$_{15}$, and the like, wherein the several R groups are as described above.

The cyclic nitroxides employed in the practice of the present invention can also have the structure:

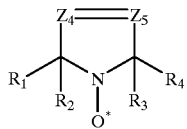

wherein $R_1$, $R_2$, $R_3$, and $R_4$ are as described above and $Z_4$ and $Z_5$, which can be the same or different, can be nitrogen or a substituted or unsubstituted carbon atom, such as =C(H)—, =C(CH$_3$)—, =C(COOH)—, =C(COOCH$_3$)—, =C(COOC$_2$H$_5$)—, =C(OH)—, =C(CN)—, =C(NR$_5$R$_6$)—, =C(CONR$_5$R$_6$)—, and the like, where $R_5$ and $R_6$ are as described above.

Another class of cyclic nitroxides that can be employed in the practice of the present invention is of the structure:

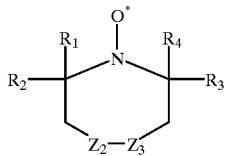

wherein $R_1$, $R_2$, $R_3$, and $R_4$ are as described above and $Z_2$ and $Z_3$, which may be the same or different, are sulfur, oxygen, primary amines, secondary amines, or substituted or unsubstituted carbon atoms, such as, >CH$_2$, >CHCH$_3$, >C=O, >C(CH$_3$)$_2$, >CHBr, >CHCl, >CHI, >CHF, >CHOH >CHCN, >C(OH)CN, >CHCOOH, >CHCOOCH$_3$, >CHCOOC$_2$H$_5$, >C(OH)COOC$_2$H$_5$, >C(OH)COOCH$_3$, >C(OH)CHOHC$_2$H$_5$, >C(NR$_5$R$_6$)—, >C(CONR$_5$R$_6$)—, >C=NOH, >C=CH—C$_6$H$_5$, >CF$_2$, >CCl$_2$, >CBr$_2$, >CI$_2$, and the like, where $R_5$ and $R_6$ are as described above.

Further, two or more nitroxyl groups can be present in the same molecule, for example, by being linked through one or more of the Z-type moieties by a linking group E, as disclosed in U.S. Pat. No. 5,254,760, which is incorporated herein by reference.

As stated above, $R_1$ and $R_4$ are independently selected from the group consisting of hydrogen, alkyl, and heteroatom-substituted alkyl and $R_2$ and $R_3$ are independently selected from the group consisting of alkyl and heteroatom-substituted alkyl. The alkyl (or heteroatom-substituted alkyl) groups $R_1$ through $R_4$ can be the same or different and preferably contain 1 to 15 carbon atoms, e.g., methyl, ethyl, propyl, butyl, pentyl, hexyl, heptyl, octyl, nonyl, decyl, undecyl, dodecyl, tridecyl, tetradecyl, pentadecyl, and the like, and isomers thereof, e.g., t-butyl, 2-ethylhexyl, and the like. It is more preferred that $R_1$ through $R_4$ be independently selected lower alkyl (or heteroatom-substituted lower alkyl) of one to four carbon atoms (e.g., methyl, ethyl, propyl, butyl, and isomers thereof). Where heteroatom substituents are present, is they can, for example, include halogen, oxygen, sulfur, nitrogen, and the like. It is most preferred that all of $R_1$ through $R_4$ be methyl.

Examples of suitable nitroxide free radical compounds that can be used in combination with the nitroaromatic compounds in the practice of the present invention, include, but are not limited to:

N,N-di-tert-butylnitroxide;
N,N-di-tert-amylnitroxide;
N-tert-butyl-2-methyl-1-phenyl-propylnitroxide;
N-tert-butyl-1-diethylphosphono-2,2-dimethylpropylnitroxide;
2,2,6,6-tetramethyl-piperidinyloxy;
4-amino-2,2,6,6-tetramethyl-piperidinyloxy;
4-hydroxy-2,2,6,6-tetramethyl-piperidinyloxy;
4-oxo-2,2,6,6-tetramethyl-piperidinyloxy;
4-dimethylamino-2,2,6,6-tetramethyl-piperidinyloxy;
4-ethanoyloxy-2,2,6,6-tetramethyl-piperidinyloxy;
2,2,5,5-tetramethylpyrrolidinyloxy;
3-amino-2,2,5,5-tetramethylpyrrolidinyloxy;
2,2,4,4-tetramethyl-1-oxa-3-azacyclopentyl-3-oxy;
2,2,4,4-tetramethyl-1-oxa-3-pyrrolinyl-1-oxy-3-carboxylic acid;
2,2,3,3,5,5,6,6-octamethyl-1,4-diazacyclohexyl-1,4-dioxy;
4-bromo-2,2,6,6-tetramethyl-piperidinyloxy;
4-chloro-2,2,6,6-tetramethyl-piperidinyloxy;
4-iodo-2,2,6,6-tetramethyl-piperidinyloxy;
4-fluoro-2,2,6,6-tetramethyl-piperidinyloxy;
4-cyano-2,2,6,6-tetramethyl-piperidinyloxy;
4-carboxy-2,2,6,6-tetramethyl-piperidinyloxy;
4-carbomethoxy-2,2,6,6-tetramethyl-piperidinyloxy;
4-carbethoxy-2,2,6,6-tetramethyl-piperidinyloxy;
4-cyano-4-hydroxy-2,2,6,6-tetramethyl-piperidinyloxy;
4-methyl-2,2,6,6-tetramethyl-piperidinyloxy;
4-carbethoxy-4-hydroxy-2,2,6,6-tetramethyl-piperidinyloxy;
4-hydroxy-4-(1-hydroxypropyl)-2,2,6,6-tetramethyl-piperidinyloxy;
4-methyl-2,2,6,6-tetramethyl-1,2,5,6-tetrahydropyridine-1-oxyl;
4-carboxy-2,2,6,6-tetramethyl-1,2,5,6-tetrahydropyridine-1-oxyl;
4-carbomethoxy-2,2,6,6-tetramethyl-1,2,5,6-tetrahydropyridine-1-oxyl;
4-carbethoxy-2,2,6,6-tetramethyl-1,2,5,6-tetrahydropyridine-1-oxyl;
4-amino-2,2,6,6-tetramethyl-1,2,5,6-tetrahydropyridine-1-oxyl;
4-amido-2,2,6,6-tetramethyl-1,2,5,6-tetrahydropyridine-1-oxyl;
3,4-diketo-2,2,5,5-tetramethylpyrrolidinyloxy;

3-keto-4-oximino-2,2,5,5-tetramethylpyrrolidinyloxy;

3-keto-4-benzylidine-2,2,5,5-tetramethylpyrrolidinyloxy;

3-keto-4,4-dibromo-2,2,5,5-tetramethylpyrrolidinyloxy;

2,2,3,3,5,5-hexamethylpyrrolidinyloxy;

3-carboximido-2,2,5,5-tetramethylpyrrolidinyloxy;

3-oximino-2,2,5,5-tetramethylpyrrolidinyloxy;

3-hydroxy-2,2,5,5-tetramethylpyrrolidinyloxy;

3-cyano-3-hydroxy-2,2,5,5-tetramethylpyrrolidinyloxy;

3-carbomethoxy-3-hydroxy-2,2,5,5-tetramethylpyrrolidinyloxy;

3-carbethoxy-3-hydroxy-2,2,5,5-tetramethylpyrrolidinyloxy;

2,2,5,5-tetramethyl-3-carboxamido-2,5-dihydropyrrole-1-oxyl;

2,2,5,5-tetramethyl-3-amino-2,5-dihydropyrrole-1-oxyl;

2,2,5,5-tetramethyl-3-carbethoxy-2,5-dihydropyrrole-1-oxyl;

2,2,5,5-tetramethyl-3-cyano-2,5-dihydropyrrole-1-oxyl;

bis(1-oxyl-2,2,6,6-tetramethylpiperidin-4-yl)succinate;

bis(1-oxyl-2,2,6,6-tetramethylpiperidin-4-yl)adipate;

bis(1-oxyl-2,2,6,6-tetramethylpiperidin-4-yl)sebacate;

bis(1-oxyl-2,2,6,6-tetramethylpiperidin-4-yl)n-butylmalonate;

bis(1-oxyl-2,2,6,6-tetramethylpiperidin-4-yl)phthalate;

bis(1-oxyl-2,2,6,6-tetramethylpiperidin-4-yl) isophthalate;

bis(1-oxyl-2,2,6,6-tetramethylpiperidin-4-yl) terephthalate;

bis(1-oxyl-2,2,6,6-tetramethylpiperidin-4-yl) hexahydroterephthalate;

N,N'-bis(1-oxyl-2,2,6,6-tetramethylpiperidin-4-yl) adipamide;

N-(1-oxyl-2,2,6,6-tetramethylpiperidin-4-yl)-caprolactam;

N-(1-oxyl-2,2,6,6-tetramethylpiperidin-4-yl)-dodecylsuccinimnide;

2,4,6-tris-[N-butyl-N-(1-oxyl-2,2,6,6-tetramethylpiperidin-4-yl)]-s-triazine;

4,4'-ethylenebis(1-oxyl-2,2,6,6-tetramethylpiperazin-3-one); and the like.

It is preferred that the nitroxyl employed in the practice of the present invention be 4-amino-2,2,6,6-tetramethyl-piperidinyloxy (4-amino-TEMPO), 4-oxo-2,2,6,6-tetramethylpiperidinyloxy (4-oxo-TEMPO), 4-hydroxy-2,2,6,6-tetramethylpiperidinyloxy (4-hydroxy-TEMPO), and/or 2,2,6,6-tetramethyl-piperidinyloxy (TEMPO).

Such stable nitroxide free radical compounds can be prepared by known methods. (See, for example, U.S. Pat. Nos. 3,163,677; 3,334,103; 3,372,182; 3,422,144; 3,494,930; 3,502,692; 3,873,564; 3,966,711; and 4,665,185; which are incorporated herein by reference.)

The nitroaromatics that may be employed are compounds having the structure:

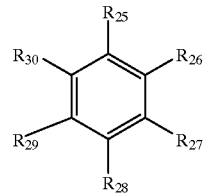

II wherein $R_{25}$, $R_{26}$, $R_{27}$, $R_{28}$, $R_{29}$, and $R_{30}$, are independently selected from the group consisting of hydrogen, alkyl, aryl, cycloalkyl, heterocyclic, substituted alkyl, substituted aryl, $OR_{11}$, $NR_{11}R_{12}$, $SR_{11}$, $NO_2$, NO, CN, $COR_{11}$, $COOR_{11}$, $CONR_{11}R_{12}$, $NR_{11}COR_{12}$, halogen (as used herein, halogen includes fluorine, chlorine, bromine, and iodine), and/or any two adjacent groups can be taken together to form ring structure(s) of five to seven members, provided that at least one of $R_{25}$, $R_{26}$, $R_{27}$, $R_{28}$, $R_{29}$, and $R_{30}$ is $NO_2$, and $R_{11}$, and $R_{12}$ are independently selected from the group consisting of hydrogen, alkyl, aryl, benzyl, cyclic, heterocyclic, and substituted alkyl or aryl where the substituents are C, O, N, S, or P, or $R_{11}$ and $R_{12}$ can be taken together to form a ring structure of five to seven members.

Preferably, the nitroaromatic contains at least one alkyl group. Such alkyl groups contain from 1 to 8 carbon atoms, such as methyl, ethyl, propyl, butyl, pentyl, hexyl, heptyl, octyl, and isomers thereof, e.g., sec-butyl, t-butyl, 2-ethylhexyl, and the like. More preferably, the alkyl group is a lower alkyl of from 1 to 4 carbon atoms. Preferably, the nitroaromatic is selected from the group consisting of: 2,6-dinitro-4-methylphenol; 2,4-dinitro-6-methylphenol; 2,4-dinitrophenol; 2,4-dinitro-6-sec-butylphenol; 2,6-dinitro-4-sec-butylphenol, 2,4-dinitro-6-sec-butylphenol, 4,6-dinitro-2-sec-butylphenol; 1,3-dinitrobenzene; 1,4-dinitrobenzene; 2-nitro-4-methylphenol; 2,4-dinitronaphthol; 2,4-dinitrochlorobenzene; and 4-cyano-2-nitrophenol; and the like.

The aromatic hydrocarbon solvent that is employed in the practice of the present invention may be any liquid aromatic hydrocarbon in which the nitroaromatic compound(s) are soluble or miscible. Illustrative of such solvents are benzene, toluene, xylene, ethylbenzene, diethylbenzene, styrene, vinyltoluene, divinylbenzene, alpha-methylstyrene and other alkylated styrenes or alkyl-benzenes, all of which materials are commercially available.

While the most preferred solvent will vary with the particular application in which the nitroxyl composition is to be employed, typically the vinyl aromatic monomer to be stabilized and its hydrogenated precursor are the preferred solvents for such applications. Thus, for the stabilization of styrene, ethylbenzene and styrene itself are the preferred solvents. Similarly for the stabilization of alpha-methylstyrene, isopropylbenzene and alpha-methylstyrene are the preferred solvents.

Typically, the weight ratio of nitroaromatic compound to aromatic hydrocarbon solvent is at least about 1:10. Preferably such ratio is between about 1:4 and about 2:1, although, as will be recognized by one skilled in the art, the preferred ratio will be dependent upon the particular components selected as well as upon the temperatures and pressures to be applied.

The compositions of this invention may be prepared by adding the desired amounts of nitroaromatic(s) and nitroxyl (s), in any order, to a measured amount of the aromatic hydrocarbon solvent. Preferably, such addition takes place under agitation.

The weight ratio of nitroaromatic compound to nitroxyl compound can be anywhere within the range of from about 99:1 to about 1:99. Preferably, the nitroaromatic:nitroxyl weight ratio is within the range of from about 99:1 to about 50:1.

The solutions prepared by the process of this invention are useful as polymerization inhibitors. When so used, they may be employed in their concentrated state or by diluting them with additional amounts of solvent so that a concentration of about 5 weight percent or less of nitroxyl is present, such dilute concentrations being readily fed into a vinyl aromatic reactor distillation column.

Among the vinyl aromatic monomers that can be polymerization-inhibited using the solutions of the present invention are: styrene, α-methylstyrene, styrene sulfonic acid, vinyltoluene, divinylbenzenes, polyvinylbenzenes, alkylated styrene, 2-vinylpyridine, and the like. Such monomers will not necessarily be stabilized indefinitely by the presence of the solution, especially when the monomers are heated as in distillation, but they can be considered to be stabilized as long as there is a measurable increase in the time for which they can be heated before the onset of polymerization.

Those skilled in the art will understand that, if desired, additional free radical scavengers can be included in the solutions that are prepared by the process of the present invention. For example, air or $O_2$, as disclosed in U.S. Pat. Nos. 5,545,782 and 5,545,786, can be added, as can the dihetero-substituted benzene compounds having at least one transferable hydrogen, e.g., a quinone derivative such as the mono-methyl-ether of hydroquinone disclosed in European Patent Application 0 765 856 A1, and other inhibitors well-known to those skilled in the art. The disclosures of the foregoing are incorporated herein by reference in their entirety.

The advantages and the important features of the present invention will be more apparent from the following example.

EXAMPLE

As a control, 4-hydroxyTEMPO was dissolved in ethylbenzene at 25° C. to form a saturated solution. The solution thus formed contained 7.0 weight percent 4-hydroxyTEMPO.

In accordance with the present invention, 4-hydroxyTEMPO was dissolved in a 1:1 blend of 4,6-dinitro-2-sec-butylphenol and ethylbenzene at 25° C. to form a saturated solution. The solution thus formed contained 13.9 weight percent 4-hydroxyTEMPO.

Substitution of 2,6-dinitro-4-methylphenol; 2,4-dinitro-6-methylphenol; 2,4-dinitrophenol; 2,4-dinitro-6-sec-butylphenol; 2,6-dinitro-4-sec-butylphenol; or 2,4-dinitro-6-sec-butylphenol for the 4,6-dinitro-2-sec-butylphenol and/or benzene, toluene, xylene, styrene, vinyltoluene, divinylbenzene, alpha-methylstyrene, or other alkylated styrenes or alkyl-benzenes for the ethylbenzene employed above will yield equivalent results.

In view of the many changes and modifications that can be made without departing from principles underlying the invention, reference should be made to the appended claims for an understanding of the scope of the protection to be afforded the invention.

What is claimed is:

1. A method for increasing the solubility of a compound having the structural formula:

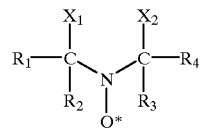

in an aromatic hydrocarbon solvent comprising adding to said solvent a nitroaromatic compound having the structure:

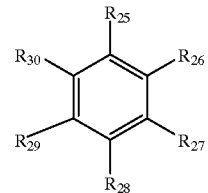

wherein there is at least one part by weight he nitroaromatic compound for every ten parts by weight of the aromatic hydrocarbon solvent, and wherein, in formula II, (1) $R_{25}$, $R_{26}$, $R_{27}$, $R_{28}$, $R_{29}$, and $R_{30}$ are independently selected from the group consisting of hydrogen, alkyl, aryl, cycloalkyl, substituted alkyl, substituted aryl, $OR_{11}$, $NR_{11}R_{12}$, $SR_{11}$, $NO_2$, NO, CN, $COR_{11}$, $COOR_{11}$, $CONR_{11}R_{12}$, $NR_{11}COR_{12}$, and halogen, (2) any two adjacent groups of $R_{25}$, $R_{26}$, $R_{27}$, $R_{28}$, $R_{29}$, and $R_{30}$ can be taken together to form ring structure(s) of five to seven members, or (3) $R_{25}$, $R_{26}$, $R_{27}$, $R_{28}$, $R_{29}$, and $R_{30}$ are combinations of (A) and(B), provided that at least one of $R_{25}$, $R_{26}$, $R_{27}$, $R_{28}$, $R_{29}$, and $R_{30}$ is $NO_2$, and $R_{11}$ and $R_{12}$ are independently selected from the group consisting of hydrogen, alkyl, aryl, benzyl, cyclic, and substituted alkyl or aryl, or $R_{11}$ and $R_{12}$ can be taken together to form a ring structure of five to seven members and, in formula I, $R_1$ and $R_4$ are independently selected from the group consisting of hydrogen, alkyl, and heteroatom-substituted alkyl and $R_2$ and $R_3$ are independently selected from the group consisting of alkyl and heteroatom-substituted alkyl; and $X_1$ and $X_2$ (1) are independently selected from the group consisting of halogen, cyano, —$COOR_7$, —S—$COR_7$, —$OCOR_7$, (wherein $R_7$ is alkyl or aryl), amido, —S—$C_6H_5$, carbonyl, alkenyl, or alkyl of 1 to 15 carbon atoms, or (2) taken together, form a ring structure of five to seven members with the nitrogen.

2. The method of claim 1 wherein the stable hindered nitroxyl compound is of the structural formula:

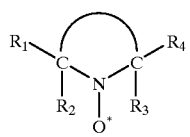

wherein $R_1$ and $R_4$ are independently selected from the group consisting of hydrogen, alkyl, and heteroatom-substituted alkyl and $R_2$ and $R_3$ are independently selected from the group consisting of alkyl and heteroatom-substituted alkyl, and the

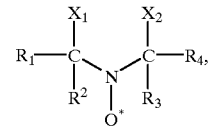

portion represents the atoms necessary to form a ring structure of five to seven members with the nitrogen.

3. The method of claim 1 wherein the nitroaromatic compound is selected from the group consisting of 2,6-dinitro-4-methylphenol; 2,4-dinitro-6-methylphenol; 2,4-dinitrophenol; 2,4-dinitro-6-sec-butylphenol; 2,6-dinitro-4-sec-butylphenol, 2,4-dinitro-6-sec-butylphenol, 4,6-dinitro-2-sec-butylphenol; 1,3-dinitrobenzene; 1,4-dinitrobenzene; 2-nitro4-methylphenol; 2,4-dinitronaphthol; 2,4-dinitrochlorobenzene; and 4-cyano-2-nitrophenol.

4. The method of claim 2 wherein the nitroaromatic compound is selected from the group consisting of 2,6-dinitro-4-methylphenol; 2,4-dinitro-6-methylphenol; 2,4-dinitrophenol; 2,4-dinitro-6-sec-butylphenol; 2,6-dinitro-4-sec-butylphenol, 2,4-dinitro-6-sec-butylphenol, 4,6-dinitro-2-sec-butylphenol; 1,3-dinitrobenzene; 1,4-dinitrobenzene; 2-nitro-4-methylphenol; 2,4-dinitronaphthol; 2,4-dinitrochlorobenzene; and 4-cyano-2-nitrophenol.

5. The method of claim 1 wherein the aromatic hydrocarbon solvent is selected from the group consisting of benzene, toluene, xylene, ethylbenzene, diethylbenzene, styrene, vinyltoluene, divinylbenzene, and alpha-methylstyrene.

6. The method of claim 2 wherein the aromatic hydrocarbon solvent is selected from the group consisting of benzene, toluene, xylene, ethylbenzene, diethylbenzene, styrene, vinyltoluene, divinylbenzene, and alpha-methylstyrene.

7. The method of claim 4 wherein the stable hindered nitroxyl compound is 4-amino-2,2,6,6-tetramethylpiperidinyloxy.

8. The method of claim 4 wherein the stable hindered nitroxyl compound is 4-oxo-2,2,6,6-tetramethylpiperidinyloxy.

9. The method of claim 4 wherein the stable hindered nitroxyl compound is 4-hydroxy-2,2,6,6-tetramethylpiperidinyloxy.

10. The method of claim 4 wherein the nitroaromatic compound is 2,4-dinitro-6-sec-butyl phenol.

11. The method of claim 4 wherein the nitroaromatic compound is 2,6-dinitro-4-sec-butyl phenol.

12. The method of claim 4 wherein the nitroaromatic compound is 4,6-dinitro-2-sec-butyl phenol.

13. In a solution consisting essentially of a solvent system and a compound having the structural formula:

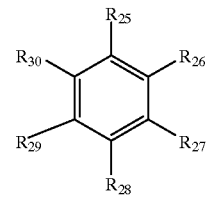

the improvement that comprises employing as the solvent system for said solution an aromatic hydrocarbon solvent and a nitroaromatic compound having the structure:

II wherein there is at least one part by weight of the nitroaromatic compound for every ten parts by weight of the aromatic hydrocarbon solvent, and wherein, in formula II, (1) $R_{25}$, $R_{26}$, $R_{27}$, $R_{28}$, $R_{29}$, and $R_{30}$ are independently selected from the group consisting of hydrogen, alkyl, aryl, cycloalkyl, substituted alkyl, substituted aryl, $OR_{11}$, $NR_{11}R_{12}$, $SR_{11}$, $NO_2$, NO, CN, $COR_{11}$, $COOR_{11}$, $CONR_{11}R_{12}$, $NR_{11}COR_{12}$, and halogen, (2) any two adjacent groups of $R_{25}$, $R_{26}$, $R_{27}$, $R_{28}$, $R_{29}$, and $R_{30}$ can be taken together to form ring structure(s) of five to seven members, or (3) $R_{25}$, $R_{26}$, $R_{27}$, $R_{28}$, $R_{29}$, and $R_{30}$ are combinations of (A) and (B), provided that at least one of $R_{25}$, $R_{26}$, $R_{27}$, $R_{28}$, $R_{29}$, and $R_{30}$ is $NO_2$, and $R_{11}$ and $R_{12}$ are independently selected from the group consisting of hydrogen, alkyl, aryl, benryl, cyclic, and substituted alkyl or aryl, or $R_{11}$ and $R_{12}$ can be taken together to form a ring structure of five to seven members and, in formula I, $R_1$ and $R_4$ are independently selected from the group consisting of hydrogen, alkyl, and heteroatom-substituted alkyl and $R_2$ and $R_3$ are independently selected from the group consisting of alkyl and heteroatom-substituted alkyl; and $X_1$ and $X_2$ (1) are independently selected from the group consisting of halogen, cyano, —$COOR_7$, —S—$COR_7$, —$OCOR_7$, (wherein $R_7$ is alkyl or aryl), amido, —S—$C_6H_5$, carbonyl, alkenyl, or alkyl of 1 to 15 carbon atoms, or (2) taken together, form a ring structure of five to seven members with the nitrogen.

* * * * *